US007122799B2

(12) United States Patent
Hsieh et al.

(10) Patent No.: US 7,122,799 B2
(45) Date of Patent: Oct. 17, 2006

(54) LED OR LASER ENABLED REAL-TIME PCR SYSTEM AND SPECTROPHOTOMETER

(75) Inventors: Huangpin Ben Hsieh, Mountain View, CA (US); Michael A. Kneissl, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 217 days.

(21) Appl. No.: 10/739,706

(22) Filed: Dec. 18, 2003

(65) Prior Publication Data

US 2005/0133724 A1 Jun. 23, 2005

(51) Int. Cl.
*G01J 5/02* (2006.01)

(52) U.S. Cl. .............................. 250/339.12; 250/458.1; 250/461.1; 250/461.2

(58) Field of Classification Search ............ 250/339.12, 250/339.06, 339.07, 458.1, 461.1, 461.2; 319/326
See application file for complete search history.

(56) References Cited

U.S. PATENT DOCUMENTS

| 5,364,790 A | | 11/1994 | Atwood et al. |
|---|---|---|---|
| 5,475,610 A | * | 12/1995 | Atwood et al. ............ 700/269 |
| 5,527,510 A | | 6/1996 | Atwood et al. |
| 5,681,741 A | | 10/1997 | Atwood et al. |
| 5,716,784 A | | 2/1998 | Di Cesare |
| 5,854,684 A | * | 12/1998 | Stabile et al. ............... 356/440 |
| 6,218,153 B1 | | 4/2001 | Sklar et al. |
| 6,346,384 B1 | | 2/2002 | Pollner |
| 6,410,223 B1 | | 6/2002 | Schaad et al. |
| 6,493,640 B1 | | 12/2002 | Clarkson et al. |
| 6,537,752 B1 | | 3/2003 | Astle |
| 6,852,986 B1 | * | 2/2005 | Lee et al. ................. 250/458.1 |
| 2002/0008871 A1 | * | 1/2002 | Poustka et al. ............. 356/317 |
| 2002/0025547 A1 | | 2/2002 | Rao |
| 2004/0023229 A1 | * | 2/2004 | Rigler ............................ 435/6 |
| 2004/0072335 A1 | * | 4/2004 | Boege et al. ............. 435/287.2 |
| 2004/0178357 A1 | * | 9/2004 | King ........................ 250/458.1 |
| 2005/0136548 A1 | * | 6/2005 | McDevitt et al. ............ 436/180 |

FOREIGN PATENT DOCUMENTS

| WO | WO 00/13018 | 3/2000 |
|---|---|---|
| WO | WO 01/29538 A1 | 4/2001 |
| WO | WO 02/12127 A2 | 2/2002 |
| WO | WO 02/14539 A1 | 2/2002 |

* cited by examiner

*Primary Examiner*—David Porta
*Assistant Examiner*—Christine Sung
(74) *Attorney, Agent, or Firm*—Fay, Sharpe, Fagan, Minnich & McKee, LLP

(57) ABSTRACT

A system for conducting a polymerase chain reaction (PCR) assay upon a collection of samples is disclosed. The PCR assay is performed by absorption detection. The system includes a multi-well plate which is adapted to retain a collection of sample wells. This system includes a thermal cycler for the multi-well plate. The system additionally includes a collection of photodetectors, and a corresponding number of light sources. The light sources are positioned such that light emitted from each of the respective light sources passes through a corresponding well retained in the multi-well plate and to a corresponding photodetector. The system also includes a processor or other means for analyzing the output signals from the photodetectors. In certain versions of the system, ultra-violet light is used.

27 Claims, 4 Drawing Sheets

LED OR LASER ENABLED REAL-TIME PCR SYSTEM AND SPECTROPHOTOMETER

BACKGROUND

The present exemplary embodiment relates to the use of absorption detection strategies in obtaining information relating to a polymerase chain reaction (PCR) assay. The present exemplary embodiment also relates to the use of light emitting diodes (LED's) or laser diodes, and particularly light sources such as these that emit light in the ultra-violet range, in spectrophotometers and for detecting polymerase chain reaction (PCR) products. The exemplary embodiment finds particular application in conjunction with real-time PCR assays, and will be described with particular reference thereto. However, it is to be appreciated that the present exemplary embodiment is also amenable to other like applications.

The polymerase chain reaction (PCR) is a powerful technique, which results in the rapid production of multiple copies of a target nucleic acid sequence. The PCR technique has made it possible to analyze DNA fragments in samples that contain amounts of DNA that are either too small, or too degraded, to permit other types of nucleic acid analysis.

The PCR method is a cycling reaction in which template DNA is denatured by heating to separate the strands of the molecule. Primer (20–30 base fragments of DNA complementary to a region of the template) is annealed to the single-stranded templates. The cycle ends as the primer molecules are elongated by the action of DNA polymerase to produce molecules that are identical copies of the original template. Because the products of one PCR cycle can act as templates for the next PCR cycle, the number of new identical molecules produced doubles with each repetition of the cycle.

PCR is an immensely valuable technique which is very widely practiced, and has revolutionized the field of molecular biology. The technique is disclosed in detail in U.S. Pat. Nos. 4,683,195; 4,683,202; 4,800,159; and 4,965,188, all of which are hereby incorporated by reference. The reaction is typically carried out in solution in small reaction vessels, where the DNA to be amplified is in suspension. Apparatuses for this process are disclosed in U.S. Pat. No. 5,038,852 and in U.S. Pat. No. 5,475,610, both of which are hereby incorporated by reference. Additional PCR references include "*PCR Protocols*: A Guide to Methods and Applications," M. A. Innis, et al., eds., Academic Press, New York, pp. 272–281; and Micklos, D. A. and G. A. Freyer, 1990, "*DNA Science*: A First Course in Recombinant DNA Technology," Carolina Biological Supply Company, Burlington, N.C. and Cold Spring Harbor Laboratory Press, Cold Spring Harbor, N.Y., all of which are hereby incorporated by reference.

PCR technology is unique in its ability to locate and exponentially amplify a small quantity of a specific nucleotide sequence which is "lost" against a large background of total nucleic acid. This feature of PCR has made possible the development of a vast number of experimental and diagnostic molecular biology techniques, which were previously extremely time consuming or, in many cases, impossible to perform.

Nucleic acids in a sample are usually first amplified by the PCR method and subsequently detected. This sequential approach is based on a single end-point measurement after the PCR is completed. The amount of amplified product observed at the end of the reaction is very sensitive to slight variations in reaction components because PCR is typically exponential. Therefore, the accuracy and precision of quantitative analysis using endpoint measurements is poor. Furthermore, endpoint measurements can produce a hook effect whereby high concentrations of a target polynucleotide to be amplified yield inaccurately low values.

In contrast to end-point determinations of amplified polynucleotides, real-time monitoring of PCR product generation offers the possibility of better precision and accuracy in quantitative measurements because the measurements are taken during the exponential phase of the PCR process. In contrast to classical end-point measurements, multiple measurements are taken during real-time monitoring. During the exponential phase of the PCR process, none of the reaction components are limiting, and therefore the effects on accuracy of reaching a maximum signal are eliminated. Real-time monitoring of PCR is based on kinetic measurements offering a better and a more complete picture of the PCR process. A number of real-time monitoring methods have been developed, however the methods use fluorescent signals in all cases.

Traditional PCR uses a thermostable DNA polymerase in a DNA synthesis reaction, primed by DNA oligonucleotides that are complementary to a specific sequence within the target DNA. Standard PCR (in the absence of probe DNA) results in a doubling of the number of copies of target sequence after each round of DNA synthesis, and a geometric increase in the number of copies after each reaction cycle. The product can be observed afterwards by separation of the DNA by agarose gel electrophoresis.

Real-time fluorescent PCR works similarly, with the addition of a third small fragment of DNA to the reaction mixture. The DNA/RNA detection reaction combines standard PCR with a third reagent, a probe DNA molecule that hybridizes to a target sequence between the sequences bound by the two PCR primers. The probe is labeled at one end with a fluorescent dye molecule and at the other end with a molecule that quenches the fluorescence of the dye molecule, such that the proximity of these two molecules results in a quenching of the dye's fluorescence. When a DNA polymerase extends one of the two primers, the probe molecule degrades and releases the fluorescent and quencher molecules bound to the ends of the probe. The separation of the dye and the quencher results in an increase in the overall fluorescence of the sample mixture. A detector in the PCR instrument continually monitors and records the fluorescence present in the sample. Significant accumulation of fluorescence in the sample above background level indicates a positive detection of the target DNA. Additional information concerning fluorescent PCR includes "Kinetic PCR Analysis: Real-time Monitoring of DNA Amplification Reactions," Biotechnology (New York), 1993, September. 11(9): 1026–30; "Simultaneous Amplification and Detection of Specific DNA Sequences," Biotechnology (New York) 1992 April, 10(4): 413–7; "Real-time Quantitative Polymerase Chain Reaction: A Potential Tool for Genetic Analysis in Neuropathology," Brain Pathol. 2002 January, 12(1): 54–66, Review; "Sensitivity of Multiplex Real-time PCR Reactions, Using the LightCycler and the ABI PRISM 7700 Sequence Detection System, Is Dependent on the Concentration of the DNA Polymerase," Mol Cell Probes, 2002 October, 16(5): 351–7; "Real Time Quantitative PCR," Genome Res. 1996 October, 6(10):986–94, all hereby incorporated by reference.

Since its inception a few years ago, real-time quantitative PCR-based assays have become an indispensable part of biological research. The fields of biotechnology and biopharmacology rely on this technology for high throughput screening of plausible genetic loci. This assay incorporates, and thus is limited by, the use of labeling fluorochromes, fluorescent primers, and Taqman probes. These fluorochromes or dye markers are expensive and their detection requires large integrated light sources and detection optics on the system. For example, an integrated real-time PCR system can cost $90,000 (Applied Biosystems ABI PRISM® 7700 Sequence Detection System) as compared to $7,500 for a non-real time PCR system (GeneAmp 9700). Both systems perform PCR amplification for 96 wellplates but the GeneAmp 9700 requires a separate spectrophotometer or a fluorescent wellplate reader for DNA concentration measurement. Accordingly, there is a need to avoid the use of fluorochromes and associated detection light sources and optics otherwise required when conducting real-time PCR analysis.

The present exemplary embodiment contemplates a new and improved spectrophotometer and PCR system, and related methods, that utilize absorption detection strategies for detecting, analyzing, or quantifying PCR products, which overcome the above-referenced problems and others. The exemplary embodiment also contemplates LED's or lasers as light sources in such devices, particularly for conducting PCR-based assays. In a particular aspect, the light is in the ultra-violet wavelength range. Additionally, the present exemplary embodiment also contemplates a new and improved real-time PCR-based assay that avoids many of the problems associated with previously known systems and techniques.

BRIEF DESCRIPTION

In accordance with an aspect of the present exemplary embodiment, a system for conducting a polymerase chain reaction (PCR) assay by absorption detection is provided. The system employs a multi-well plate adapted for retaining a collection of sample wells. The system also comprises a thermal cycler in thermal communication with the multi-well plate. The system additionally comprises at least one photodetector that provides an output signal. The system further comprises at least one light source which is positioned such that light emitted therefrom passes through a corresponding well retained in the multi-well plate, and to a corresponding photodetector. The system further comprises a means for analyzing the output signals from the one or more photodetectors, and determining information indicative of the polymerase chain reaction by absorbance detection.

In accordance with a further aspect of the present exemplary embodiment, a system for conducting a polymerase chain reaction assay is provided that utilizes ultra-violet light. The system comprises a multi-well plate in which the plate is adapted to retain a plurality of sample wells. The system also comprises a thermal cycler in thermal communication with the multi-well plate. The system further comprises a collection of photodetectors, in which each photodetector provides an output signal. The system also comprises at least one ultra-violet light source. The ultra-violet light source is positioned such that light emitted therefrom passes through a corresponding well retained in or otherwise provided by the multi-well plate and to a corresponding photodetector of the collection of photodetectors. The system also includes a processor or other means for analyzing the output signals from the plurality of photodetectors.

In accordance with another aspect of the present exemplary embodiment, a spectrophotometer is provided for measuring the intensity of ultra-violet light utilizing a particular sample well configuration. The spectrophotometer comprises a sample well adapted for retaining a liquid sample. The sample well has a first region and a second region in fluid communication with the first region. The spectrophotometer also comprises a photodetector. Additionally, the spectrophotometer includes a first ultra-violet light source that is positioned relative to the sample well and the photodetector such that the ultra-violet light emitted from the first light source passes through the first region of the sample well to the photodetector. The spectrophotometer also includes a second ultra-violet light source positioned relative to the sample well and the photodetector such that ultra-violet light emitted from the second light source passes through the second region of the sample well to the photodetector.

In a further aspect of the exemplary embodiment, a method of performing a polymerase chain reaction assay by absorbance detection is provided. The method comprises providing a system that includes a multi-well plate, a thermal cycler, a photodetector that provides an output signal, at least one light source positioned to pass light through the multi-well plate and to the photodetector, and a means for analyzing the output signal of the photodetector. The method also comprises obtaining samples upon which the polymerase chain reaction assay is to be performed. Additionally, the method comprises depositing samples in the multi-well plate. And, the method comprises performing a polymerase chain reaction in the samples. The method includes emitting light from the light source(s) such that light passes through the samples to the photodetector. And, the method comprises analyzing the output of the photodetector to determine the absorbance of light and information indicative of the polymerase chain reaction.

In accordance with yet another aspect of the present exemplary embodiment, a method of performing a polymerase chain reaction assay is provided. The method is based upon using ultra-violet light as follows. The method includes providing a system including (i) a multi-well plate adapted to retain a plurality of samples, (ii) a thermal cycler, (iii) a photodetector that provides an output signal, (iv) a plurality of ultra-violet light sources positioned such that light emitted therefrom passes through the multi-well plate to the photodetector, and (v) a means for analyzing the output signal of the photodetector upon detecting ultra-violet light. The method also comprises obtaining samples upon which the polymerase chain reaction assay is to be performed. The method further comprises depositing the samples in the multi-well plate. The method also comprises performing a polymerase chain reaction in the samples. The method further comprises emitting ultra-violet light from the plurality of ultra-violet light sources such that the light passes through the samples to the photodetector. The method also includes analyzing the output signal of the photodetector.

One advantage of the present exemplary embodiment is the provision of a PCR system and related assays and techniques that do not require the use of fluorochromes and associated detection light sources and optics otherwise required.

Another advantage of the present exemplary embodiment is to reduce or entirely avoid the cost of fluorescent primers and Taqman probes utilized with many real-time PCR systems.

Still further advantages and benefits of the present exemplary embodiment will become apparent to those of ordinary skill in the art upon reading and understanding the following detailed description of the preferred embodiments.

BRIEF DESCRIPTION OF THE DRAWINGS

The exemplary embodiment may take form in various components and arrangements of components, and in various steps and arrangements of steps. The drawings are only for purposes of illustrating preferred embodiments and are not to be construed as limiting the exemplary embodiment.

DETAILED DESCRIPTION

Figure 1:
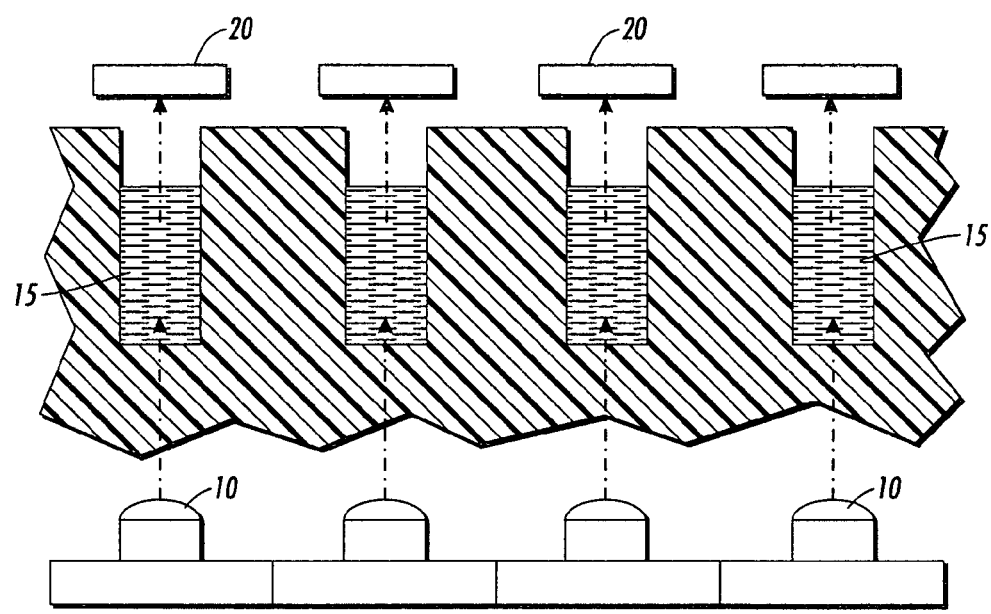
FIG. 1 is a schematic illustration of a plurality of UV light sources, wells, and photodetectors in the present exemplary embodiment PCR system.

Nucleic acids strongly absorb light having a wavelength of 260 nm. Short oligomers, long-chain DNA (full length PCR products), and RNA all absorb differently at 260 nm. By utilizing 260/280 nm absorption ratios on an amplified nucleic acids/enzyme mixture, one can quantitatively determine the PCR product concentration as well as purity. The present exemplary embodiment integrates an array of ultra-violet light sources and an array of photodetectors in a PCR instrument to quantitatively measure the absorption of 260/280 nm light by amplified materials in a multiwell plate in real-time. The ultra-violet light source can be an LED, and will be described herein as such. The term "ultra-violet" light as used herein generally refers to light having a wavelength of from about 100 nm to about 400 nm, particularly from about 175 nm to about 350 nm, and more particularly from about 240 nm to about 300 nm. In certain applications described herein, the ultra-violet light has a wavelength of 260 nm or 280 nm. And, in certain applications, ultra-violet light is utilized having a wavelength of 260 nm concurrently with ultra-violet light having a wavelength of 280 nm. It will be appreciated that in the applications described herein, although a single wavelength value is given, in actuality, light having a range of wavelengths is emitted.

Typical real-time quantitative PCR systems such as the Applied Biosystems ABI PRISM® 7700 Sequence Detection System integrate a 96 well thermal cycler, a laser to induce fluorescence, a CCD (charge-coupled device) detector, and sequence detection software. In order to read from all samples in the plate, the laser individually addresses each and every well of the plate. An optical fiber inserted through a lens is positioned over each well, and laser light is directed through the fiber to excite the fluorochrome in the PCR solution. Emissions are sent through the fiber to the CCD camera, where they are analyzed by the software's algorithms. Collected data are subsequently sent to the computer. Emissions are measured every 7 seconds. A system such as this which integrates such scanning optics is large and expensive. It will be appreciated that some PCR systems utilized for quantitative assays, use a photomultiplier tube (PMT) in addition or instead of a CCD camera. The present exemplary embodiment can be utilized in conjunction with systems using PMT's.

A typical DNA concentration measurement is performed on a spectrophotometer such as the DU 530 Life Science Spectrophotometer from Beckman Coulter. That instrument utilizes a fixed deuterium lamp and a monochromometer to provide a single wavelength light source and measurement from 190 to 350 nm. Nucleic acid samples prepared in a quartz cuvette are positioned in the light path and the absorption of 260 nm light is determined. The disadvantage of this unit is the throughput rate. Using a fixed lamp and a single detector, the measurement is limited to one sample at a time. Even with a rotating cell module, it is still limited to a few samples per loading.

Artisans who perform a PCR amplification of a plate on a PCR machine such as the previously noted lower cost GeneAmp 9700 model would either have to remove the samples well-by-well to determine the concentration on a spectrophotometer or use fluorescence detection and read the sample on a dedicated fluorescence plate reader. Those dedicated fluorescence plate readers are also bulky and expensive.

The present exemplary embodiment integrates the detection optics of a spectrophotometer with a lower-cost plate-based PCR system such as the GeneAmp 9700 model. The overall cost of the resulting integrated system is relatively low, e.g. less than about $15,000. Specifically, the exemplary embodiment provides a PCR-based assay utilizing absorption detection strategies. This novel approach represents a significant advance in the art as it eliminates the need for fluorescing agents or other light producing agents in the PCR for monitoring aspects of the reaction or the end products thereof.

In the exemplary embodiment, in order to avoid the bulky size of conventional scanning optics, an array of inexpensive ultra-violet LED's, emitting 260 nm and 280 nm wavelength light are incorporated in a PCR system with the format of a wellplate. The arrays of emitter and detectors have a configuration like that in FIGS. 1 and 2. Specifically, referring to FIG. 1, the exemplary embodiment provides a plurality of ultra-violet light emitting units, such as LED's, designated as 10. The array of ultra-violet LED's 10 are positioned with respect to a plurality of wells 15, such that light emitted from each LED 10 travels through a corresponding well (and sample contained therein), to a corresponding photoreceptor or photodetector 20. Optical filters could be used, either placed at the input of the photodetector or at the output of the LEDs/lasers or both to suppress any unwanted light (e.g. light emitted by the LED aside from the center wavelength peak). For example, LEDs sometimes exhibit luminescence at longer wavelengths from recombination through defects in the LEDs active regions or recombination of carriers outside the active region of the LED. This unwanted luminescence is typically 3–4 orders smaller than the main luminescence peak. Nevertheless it may be desirable to suppress this luminescence even further by using optical band-pass filters.

Since the footprint of an LED or laser diode is very small, multiple LEDs or lasers of different wavelength could be integrated into a single package or several packaged LEDs/laser can be very closely spaced to excite one well-plate. The LED 10 could actually represent several LEDs with different wavelengths, but very closely spaced. For example, LED 10 could contain a 260 nm and a 280 nm LED. To perform an absorbance measurement, first the 260 nm LED would be turned on and the absorbed light at 260 nm detected by the photodetector. The 260 nm LED would be turned off and then the 280 nm would be turned on and the absorbed light at 280 nm detected by the photodetector. These measurements could be performed very quickly after each other since they do not require any physical movement of the sample. LEDs can be turned on and off very quickly. Turn on/off times for LEDs are typically on the order of a few nanoseconds or tens of nanoseconds. Laser diodes are even faster with sub nanosecond switching times.

Figure 2:
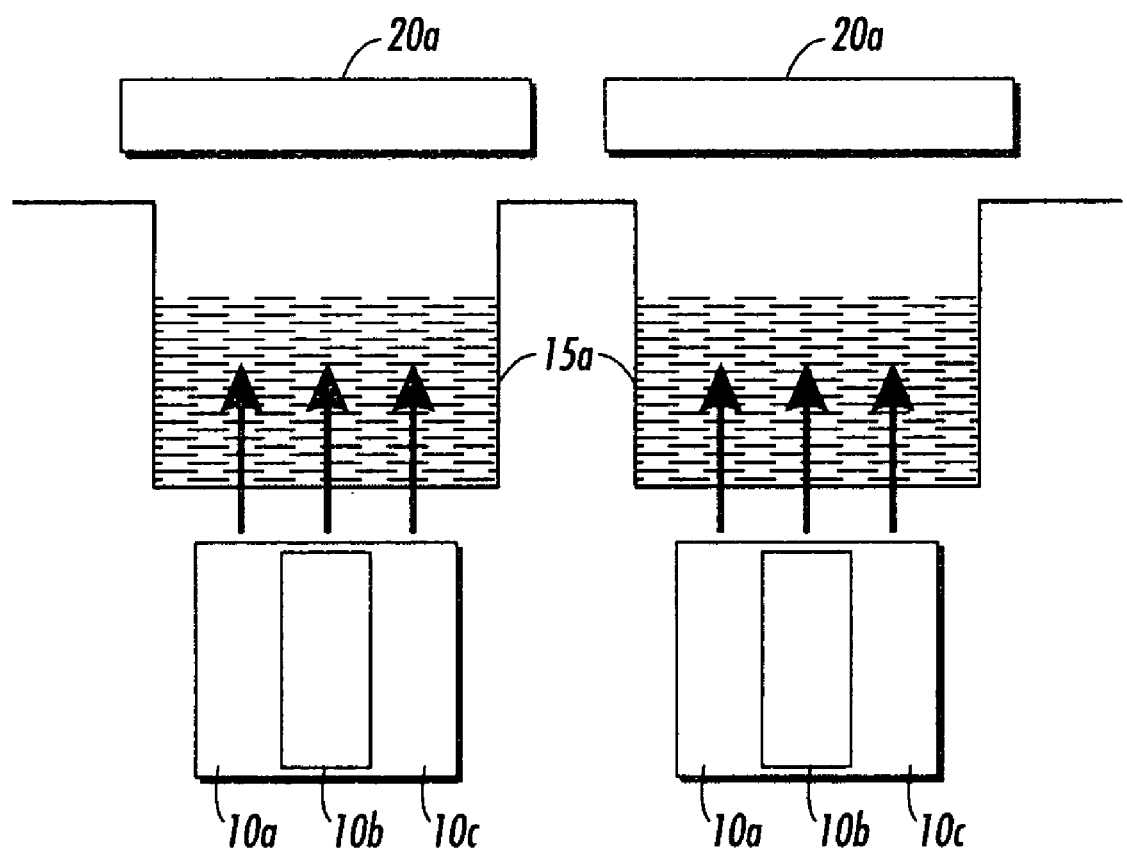
FIG. 2 is a schematic illustration of a configuration of a plurality of closely spaced multiple wavelength light sources and a well.

FIG. 2 illustrates a configuration of closely spaced light sources 10a, 10b, and 10c, which are dedicated to a corresponding well 15a and a photodetector 20a. Each of the light sources 10a, 10b, and 10c can be an LED or a laser diode. Other light sources can be utilized. Furthermore, the number of light sources used in association with each well may vary. The configuration of FIG. 2 can operate as follows. LED 10a is activated to emit light of a first wavelength or first set of wavelengths. Corresponding light is detected by the appropriate photodetector 20a and then, or concurrently, the LED 10b is activated. The LED 10b emits light having a different wavelength or set of wavelengths from LED 10a. The light is detected by the appropriate photodetector 20a. The LED 10b is de-activated and then, or concurrently, the LED 10c is activated. The LED 10c emits light having a different wavelength or set of wavelengths from LED 10a and LED 10b. The light is detected by the photodetector 20a. As previously noted, this series of measurements are performed very rapidly. The collection of closely spaced light sources, such as 10a, 10b, and 10c, can be configured to sequentially emit light as described.

Figure 3:
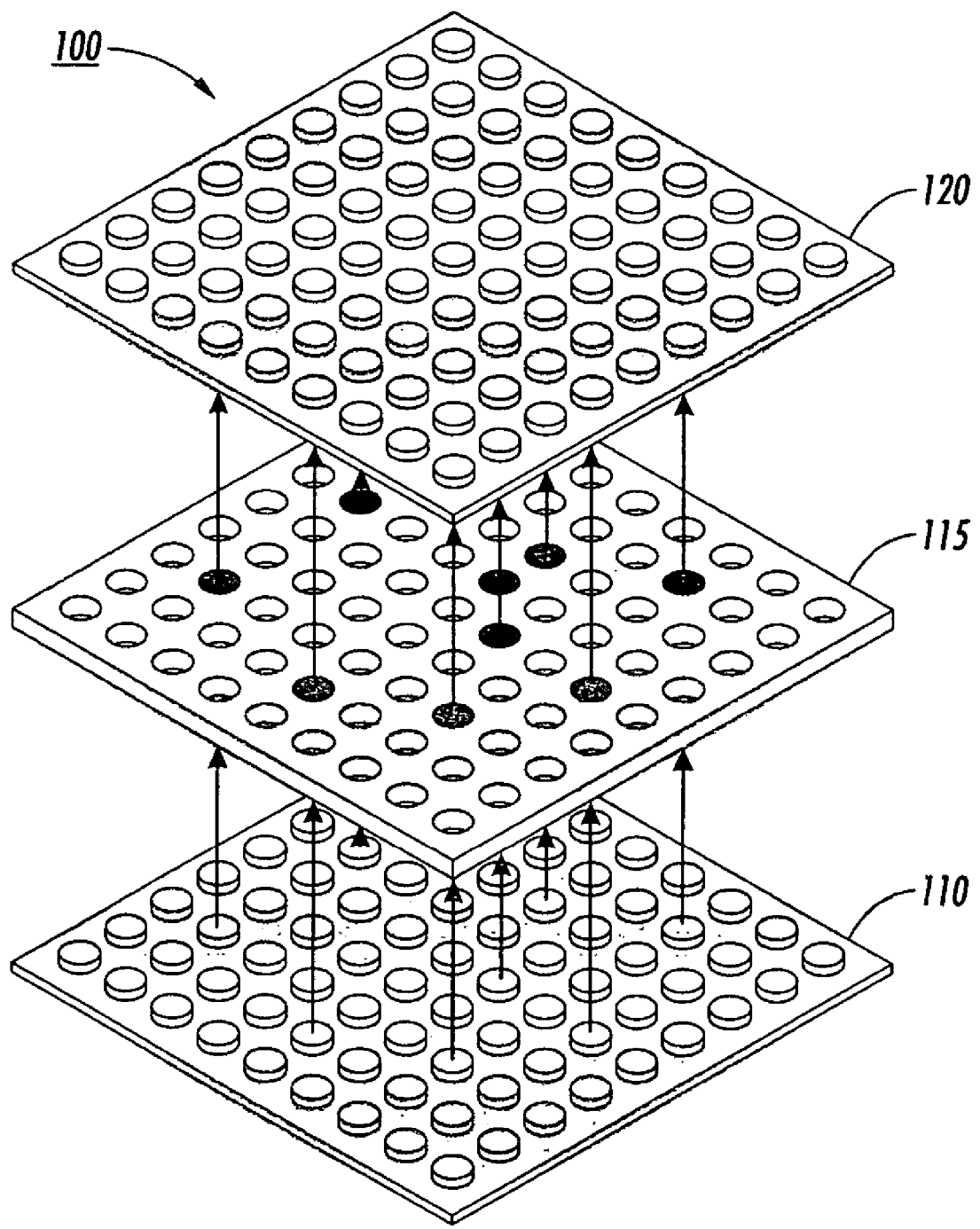
FIG. 3 is a schematic illustration of arrays of UV light sources, wells, and detectors as used in conjunction with the present exemplary embodiment PCR system.

FIG. 3 illustrates a system 100 of an array of ultra-violet light sources 110, an array of wells 115, and an array of photodetectors 120. It will be understood that the light source array 110 includes a plurality of ultra-violet light sources disposed on a suitable substrate or mounting component and arranged in a particular configuration, which typically is a grid pattern. The well array 115 comprises a plurality of sample wells, also supported and positioned on or within a suitable retaining substrate. The photodetector array 120 includes a plurality of photodetectors similarly mounted and arranged to receive light emitted from a respective light source from the array 110 and which light has passed through a respective well of the array 115. The system 100 can be readily incorporated into a commercially available plate-based PCR system.

Figure 4:
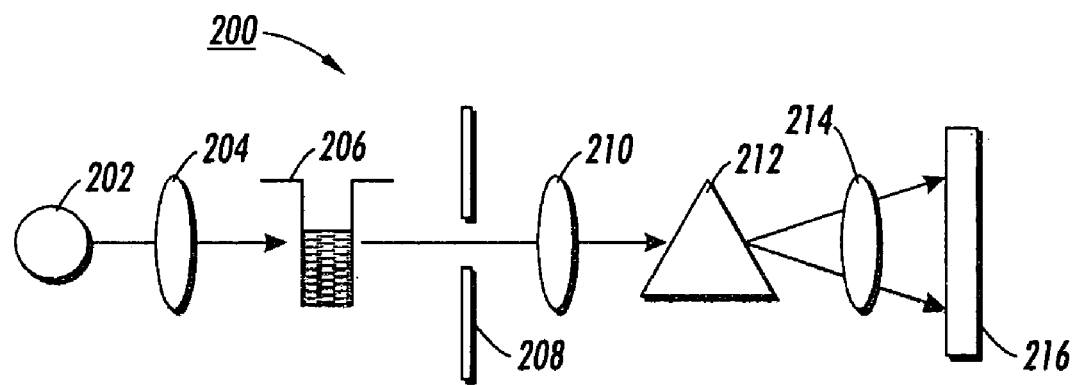
FIG. 4 is an illustration of a spectrophotometer configuration.

Currently, spectrophotometers may utilize deuterium lamps or xenon flash lamps as light sources and a grating configuration for wavelength selection. A typical system 200 is shown in FIG. 4. A light source 202 emits light directed toward a first lens 204. Light passes through the first lens 204 to a sample well 206. Light passes through the well 206 and sample contained in the well, and then through a slit 208. Light continues and passes through a second lens 210. The light continues and passes through a grating element 212 which may be in the form of a prism. The grating element 212 is utilized to select the particular wavelength of light desired, which is then directed to a third lens 214. The light continues and is directed to a photodetector 216. Other systems use combinations of optical filters to select a certain wavelength. In all cases the systems are very complex and render the entire system expensive.

The present exemplary embodiment of a PCR system utilizing ultra-violet light sources and particularly the use of LED for the emission of such light, provides new possibilities and applications. A particular type of an ultra-violet LED light source contemplated for use in the exemplary embodiment is a GaN-based ultra-violet LED. The current highest reported output power for such LED's is about 0.15 mW at 285 nm. However, it is expected that prototypes of 280 nm and 260 nm LED's will become available in the next two years. Significant research efforts are underway concerning the development of high power ultra-violet LED's and laser diodes for bio-agent detection systems. The target wavelength is about 280 nm with output powers in the range of 10–100 mW per LED.

The use of ultra-violet LED's for detecting PCR products (260 nm and 280 nm) has never been proposed before. This is the first time such low-cost alternative to laser or scanning optics is envisioned, largely due to the unavailability of such LED's in the past.

Some of the advantages of ultra-violet LED's for spectrophotometers or in-situ DNA/RNA concentration measurements in PCR systems are as follows.

A single wavelength emission is utilized. No additional grating or filter or complex optics are required to select the desired wavelength and focus the light. That significantly simplifies the experimental setup and reduces the cost of assembly. For example, the cost for high performance optical filters in the ultra-violet range are in the hundreds of dollars range. The prices are similar for ultra-violet lenses and for grating or prism assemblies. Again, it will be appreciated that in the applications and systems described herein utilizing a single wavelength of light, e.g. 260 nm, the UV LED component actually emits a relatively narrow range of wavelengths generally centered about the reported wavelength. For example, for a primary emission of 260 nm, there will likely be emitted light with a wavelength of about 5 to 10 nm greater or lesser than the primary emission.

Another advantage is the low cost of ultra-violet LED's. Semiconductor LED's can be mass-produced and made extremely inexpensive. Current GaN-based violet, blue and green LED's cost on the order of 10 to 50 cents per packaged device and a similar price range is to be expected for future mass-produced GaN-based ultra-violet LED's. For PCR systems, a combination of 260 nm and 280 nm LED's can be used to satisfy the system requirements. Multiple wavelength LED's can be either integrated as hybrid LED chips or special LED's could be developed, whose emission can be switched between two or more wavelengths.

Yet another advantage relates to the high output power of ultra-violet LED's. Ultra-violet LED's output power levels in the range of 10 mW are within reach in the near future. This is significantly higher than the power levels obtained by deuterium lamps, which have a typical output power of about 1 mW at 260 nm (for an sampling area of 5 mm diameter and FWHM of about 2 nm). In addition, the brightness of ultra-violet LED's or laser diodes is much higher. The typical footprint of an LED is 200 μm×200 μm, which means that the light intensity can be concentrated to a smaller area and reduces the amount of additional optics (e.g. lenses) needed to concentrate the light. That is a considerable advantage for high throughput PCR systems with a large number of wells per plate (96, 384, or 1536 wells) and consequently smaller wells. The footprint for a well of a 96 well plate is about 3 to 4 mm in diameter for each well with a height between 1 to 5 mm (for 10 to 60 μL volume). The footprint of a 384 wellplate system is about 2.5 mm in diameter for each well for volumes of 5 to 15 μL. Those dimensions are still large enough to fit several LEDs in the area of a single well in a wellplate. In contrast, conventional PCR systems using deuterium lamps will encounter increasingly larger problems focusing the light to a smaller and smaller spot size.

Furthermore, another advantage relates to LED arrays. Multiple LED's can also be arranged in one- or two-dimensional LED arrays. This enables the measurement of the absorption in multiple wells at the same time. Massive parallel processing significantly reduces the measurement time and accelerates the throughput. This can be a significant cost/time factor in the operation of a PCR system, particularly with the trend going to higher-density wellplates. For example, each temperature cycle in a PCR system takes about 1 to 3 minutes to complete. A typical PCR reaction completes in the order of 30 to 40 cycles to amplify and obtain a relevant amount of materials. Assuming the time it takes to measure the DNA concentrations in-situ after each cycle with a single light source (e.g. Argon laser) is 0.1*N seconds, N being the number of wells in a wellplate, for a 384 wellplate this would translate into an extra 38 seconds of measurement time per cycle. Similarly, it would take much longer for higher density plates and could affect the accuracy of the readouts as sample amounts have changed over this period of time. Measuring all 384 or 1536 wells in parallel, which can be easily implemented using LED and photodetector arrays, would reduce this time to a negligible amount.

Moreover, another advantage of ultra-violet LED's is that these light sources can be pulsed. In order to avoid bleaching or heating of the DNA molecules; short, but intense pulses can be produced by LED's. LED's can be turned on and off in a very short time scale (about 1 ns to 100 ns), depending on the design, the size and the packaging of the LED. The LED pulses can also be synchronized with a photodetector readout using common Lockin techniques to achieve better signal to noise ratios and higher sensitivity ranges. In addition, LED's do not require any warm-up time before stable light output is achieved. This is in contrast to deuterium and Xenon lamps, which require at least several minutes of warm-up time, before stable operation is achieved.

Yet another significant advantage in using an LED ultra-violet light emitting source is the relatively long operating lives of such components. It is believed that the operating life of an ultra-violet LED may be as long as 10,000 or more hours. The use of these light sources would eliminate replacement of the LED in most systems.

The following is intended to give an estimate of the sensitivity of a PCR system using ultra-violet LED's as light sources.

Concentration Measurements:

According to Lambert-Beer's law the transmitted light intensity $P_t$ going through a sample with a concentration c is:

$$P_t = P_o * 10^{-\epsilon cx}$$

where Po is the incident light intensity, $\epsilon$ is the Molar extinction coefficient and x the optical path length.

The absorbance A is defined as:

$$A = \log(P_o/P_t) = \epsilon cx$$

For DNA or RNA strands of the length L, the molecular extinction coefficient $\epsilon$ is approximately:

$$\epsilon \sim L*10000 \text{ liter/mole/cm}$$

For example, at a wavelength of 260 nm and for an absorption length x=10 mm, the absorbance for single-stranded (ss) DNA, double-stranded (ds) DNA and RNA is equal to 1 for the following concentrations:

| | |
|---|---|
| ds DNA | A = 1 for c = 50 µg/ml |
| ss DNA | A = 1 for c = 33 µg/ml |
| RNA | A = for c = 40 µg/ml |

For in-situ measurements of the DNA or RNA concentrations in a PCR, the liquid level in the well will define the optical path length of the system. Current PCR systems employ 96 well plates with volumes ranging between 10 and 60 µL and well diameters of 3 to 4 mm. Consequently, the liquid levels are in the range between 1 and 5 mm. Newer PCR systems employ 384 well plates with volumes ranging between 5 and 15 µL and typical diameters of 2.5 mm. The liquid levels and, for a vertical configuration, the optical path lengths are in the range between 1 and 3 mm. In order to increase the optical path length, narrower wells with higher liquid levels could also be used. Well plates with multiple/variable well depths can be designed to increase the dynamic range and/or accuracy of the measurements. This is illustrated in FIG. 4. Liquid levels also can be an input from the user or alternatively an automatic liquid sensing mechanism can be implemented.

Detection Limits of Ultra-Violet Led's Combined with Photodetectors:

The output power PLED of ultra-violet LED's is anticipated to be at least 1 mW. The optical throughput ηopt of the LED/sample/photodetector assembly is estimated to be about 10%. The sensitivity of an ultra-violet-enhanced Si photodiode or Si CCD array is about ηPD=0.05 A/W. As a consequence, the photocurrent induced in the Si photodetector with an LED of 1 mW output power and no absorption in the sample will be:

$$I_{det} = \eta_{PD} \times P_{LED} = 5*10^{-6} A = 5 \mu A$$

The dark current of a Si photodiode is about 1 pA or smaller, which means that the dynamic range of an ultra-violet LED-based PCR system should be about 6 orders of magnitude. Since A=1 equals one order of magnitude of attenuation of the signal, the measurable absorbance range of such a LED-based system would be between A=0 to A=6. With A=εcx, the concentrations one could detect with such a setup would range between c=0 and c=300 µg/ml fords DNA, assuming an optical path length of 10 mm.

By using higher power ultra-violet LED's, this range could be further extended. Improved sensitivity ranges could also be achieved by using III–V based photodetectors, like GaAs, InGaP or GaN with lower dark currents and higher sensitivities in the ultra-violet range. Avalanche photodiodes, e.g. SiC, GaN, GaAs or Si could also be used. The sensitivity of avalanche photodiodes is much greater than simple photodiodes because the signal is amplified by the avalanche process. Avalanche photodiodes have a typical gain of between 10 and 10000, which means that the signal is amplified by a factor of 10 to 10000. This increase in sensitivity would translate into an increase in the dynamic range of the in-situ PCR system. Drawbacks of using avalanche photodiodes are their higher cost and that the noise level in the measurement also increases. Using improved measurement techniques like Lockin amplifiers can also extend the dynamic range of the measurements. For example, by using a 100 mW ultra-violet LED with a GaN photodetector (ηPD=0.2 A/W), the detector photocurrent without attenuation would be Idet=2*10–3 A=2 mA. With dark currents of GaN photodiodes of about 1 pA, the dynamic range of an ultra-violet LED-based PCR system should be about 9 orders of magnitude and the absorbance range of such an LED-based system would be between A=0 to A=9. This translates into double-stranded DNA concentrations from 1 to 450 µg/ml. This is superior to most fluorescence-based detection systems, as their dynamic ranges typically do not exceed 5 to 6 orders of magnitude.

Figure 5:
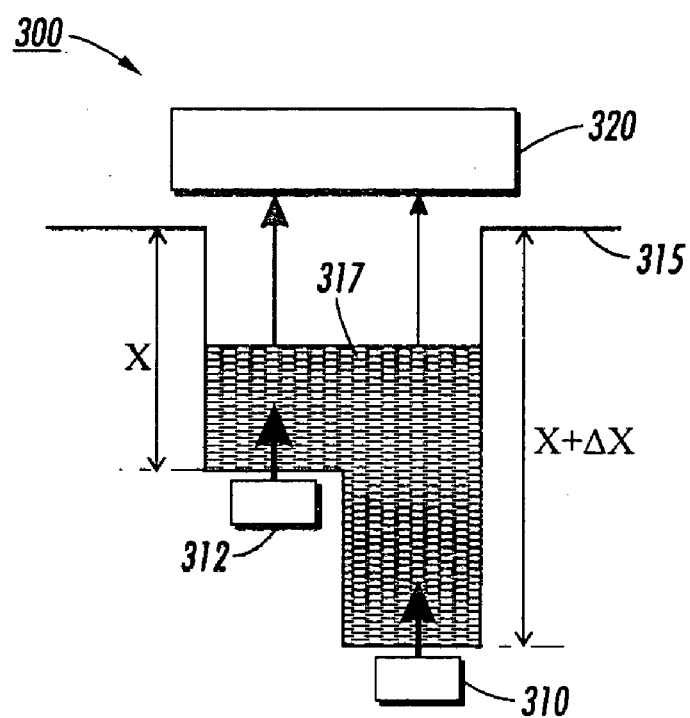
FIG. 5 is a schematic illustration of an exemplary embodiment well design that enables variable absorption lengths.

FIG. 5 illustrates an improved well design in accordance with the exemplary embodiment to enable variable absorption lengths for improved quantitative analysis of DNA concentrations. This configuration allows measuring the DNA concentrations over a wider dynamic range, e.g. higher concentrations with shorter absorption length, lower concentrations with longer absorption length. It also could lead to a more accurate determination of DNA concentrations by using one of the transmission measurements as reference and thereby eliminating the necessity to determine the absolute light output $P_0$ from the LED. The concentrations are then determined from the ratio between the transmitted power $P_1$ going through path x and the transmitted power $P_2$ going through path $x+\Delta x$ using the following relationship:

$$c = \epsilon^{-1} * \Delta x^{-1} * \log(P_1/P_2)$$

Specifically, the system 300 shown schematically in FIG. 5 includes a plurality of ultra-violet light sources, such as a first ultra-violet LED 310 and a second ultra-violet LED 312. The system 300 also includes a well 315 defining at least two regions that provide different path lengths for ultra-violet light traveling through the well 315. In the system 300 depicted in FIG. 5, the well 315 contains a liquid sample 317. The well 315 is configured such that when a liquid sample is deposited therein, two different depths or liquid sample heights result, i.e. x and $x+\Delta x$. The system 300 also comprises a photodetector 320. The photodetector 320 is positioned with respect to the well 315 and the ultra-violet light sources 310 and 312 such that the photodetector receives light emitted from each of the light sources 310 and 312 after such light has passed through the different regions of the well 315.

Another exemplary embodiment described herein relates to the use of an ultra-violet laser as a light source in a PCR based assay system. Instead of an ultra-violet LED light source as described herein, an ultra-violet laser light source can be utilized.

In general, ultra-violet semiconductor laser diodes can provide similar advantages for a real-time PCR system as discussed for the case of ultra-violet LED's. However, the design and fabrication of ultra-violet laser diodes is more sophisticated compared to LED's. Nevertheless, a number of the performance parameters of laser diodes are actually superior to LED's and therefore the use of an ultra-violet laser, instead of ultra-violet LED's in a real-time PCR system can improve the overall system performance, without necessarily adding to the overall costs. The following is a listing of numerous performance parameters comparing ultra-violet LED's and ultra-violet laser diodes.

The spectral emission of laser diodes is very narrow. Typically, the emission is less than 0.1 nm for Fabry-Perot type lasers and even smaller for DFB or DBR lasers. Therefore, the signal to noise ratio in the absorption measurements would be improved. In comparison, the FWHM of an ultra-violet LED is expected to be in the order of 5 nm. In addition, the emission of laser diodes is more directional, which means that the laser beam can be more easily directed and concentrated into the absorbing volume of the well.

Concerning cost, typically LED's are less expensive than laser diodes, because their design and fabrication requires less sophistication. On the other hand, mass-produced laser diodes can also be made relatively inexpensive, as has been demonstrated in other semiconductor materials. For example, IR laser diodes for CD players are typically about $1/piece in large volumes and similar prices are approached for red lasers for DVD systems. In comparison, current GaN-based violet, blue and green LED's cost in the order of 10 to 50 cents per package device and a similar price range is to be expected for future mass-produced GaN-based ultra-violet LED's. On the other hand, some of the additional cost for laser diodes might be outweighed by the performance improvements and potential cost reductions in other system components.

Regarding power output and current characteristics, laser diodes are typically more efficient than LED's. Therefore, for a given input current level, the output power of a laser is larger than those achieved with LED's. Output power levels for lasers in the range of 10 mW to 100 mW are anticipated. In addition, the output power of a laser diode can be more effectively concentrated and directed to the sample volume of interest, because the laser emits a more directional beam and the cross section of the lasing area (looking at the front output mirror) is very small (1–2 square microns). Furthermore, the light output versus current characteristic of a laser diode is very linear above threshold. This could help to improve measurement accuracy, e.g. by measuring the relative absorption (from the relative transmission changes) for different laser current, i.e. laser power, levels.

Concerning size, the typical footprint of an LED is similar to a laser diode, although the more sophisticated packaging of a laser diode might lead to a larger footprint for the package device.

As to arrangements, multiple lasers can also be arranged in one- or two-dimensional laser arrays the same way LED's can be. The somewhat higher cost of laser diodes would of course also translate into higher cost for these laser arrays.

Concerning multi-wavelength operation, laser diodes emitting at different wavelengths can be closely spaced similar to what can be achieved for LED's. This can be done in a hybrid fashion, by placing two different wavelength laser chips side-by-side or alternatively, multi-wavelength ultra-violet laser diodes can be integrated on a single chip.

Regarding pulsed operation, such is possible for laser diodes as well as for LED's. The modulation speed for laser diodes is actually even faster than for LED's. For direct current modulated laser diodes, rise and fall times on the order of 0.1 to 1 ns are typical. In addition, mode-locked or q-switched laser diodes are capable of generating extremely short (about 1 to 20 ps) optical pulses of high intensity (hundreds of mW to tens of Watts). Such power levels and time constants might enable not only improved transmission measurements, but also totally different concentration measurement modes based on direct excitation of fluorescence in proteins and DNA/RNA.

The LED or laser light sources described herein can be nearly any type of device such as, but not limited to, organic light emitting diodes, semiconductor light emitting diodes, laser diodes, solid state laser diodes, and combinations thereof.

Furthermore, the systems and methods of the exemplary embodiment can be configured such that more than a single wavelength of range of wavelengths are utilized. That is, techniques or assays using several wavelengths or range of wavelengths concurrently can be employed.

Moreover, the physical arrangement of the light sources in the exemplary embodiment is not limited to the arrangements described and depicted herein. That is, the exemplary embodiment includes systems in which a light source may be positioned transversely to the sample or well, and directed via an optical element such as mirrors, reflectors, wave guides, optic tubes, or fiber optics, to the desired orientation or location. It may in some applications be less expensive to utilize a single light source, and then distribute light emitted therefrom to multiple locations, such as adjacent multiple sample wells. A bundle of fiber optic lines can be employed for such an application.

In addition to absorption-based nucleic acids detection, an ultra-violet LED or laser enabled real-time quantitative PCR system is also compatible with fluorescent detection and can be implemented that way. Additional filters (emission and/or excitation) can be implemented with the arrays of photosensors and/or LED/LD emitters. Many fluorescent tags that work with lasers at visible wavelength can also be efficiently excited directly with ultra-violet (200–400 nm) light or indirectly with fluorescent resonance energy transfer (FRET). Since the footprint of an LED or laser diode is very small, multiple LEDs or lasers of different wavelengths could be integrated into a single package or several packaged LEDs/laser can be very closely spaced to excite one well-plate. The emission wavelength of LEDs can range from the UV to all the visible wavelength and infrared (IR). By combining multiple wavelength LEDs/lasers, the system could not only be used for in-situ concentration measurements by UV absorbance, but also excite fluorescent tags of all kinds for additional analysis.

In addition to the absorption-based nucleic acids detection, these UV LED or laser diodes are also compatible with fluorescent detection and can be implemented that way. Arrays of LED/laser diode emitters can replace a scanning laser and enable simultaneous detection of multiple sites, such as those in a multi-well plate. This reduces the time associated with scanning and thus could provide significant benefits. Many organic fluorescent dyes or inorganic semiconductor quantum dots that work with lasers at visible wavelength are also sufficiently excited by such UV (200–400 nm) LED or laser diodes. Fluorescent resonance energy transfer (FRET) is another application where dyes that emit at longer wavelength can receive the emitted energy and be excited from cognate dyes that are excited by shorter wavelength such as the UV LEDs and LDs. The system described herein includes an array of light sources and an array of photodetectors configured to measure the absorbance or fluorescence signal from a collection of wells, in parallel.

Although not wishing to be bound to any particular theory, it is believed that conducting a PCR-based assay using absorbance detection provides numerous advantages as compared to conducting such assays via fluorescent-based detection strategies. Generally, absorbance-based measurements may be made across a relatively broader dynamic range as compared to fluorescent-based detection methods.

The exemplary embodiment although directed to the use of ultra-violet light, is in no way limited to this range of wavelength. That is, the embodiment includes systems and assays that utilize light having a wavelength outside of the ultra-violet range. Furthermore, the exemplary embodiment includes systems in which the photodetector is configured to detect light having a wavelength different than that emitted from the light emitting diode or laser light source. For example, the light source can emit light that excites reaction species in the sample that in turn emit light of a different wavelength.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

We claim:

1. A system for conducting a polymerase chain reaction assay upon a plurality of samples by absorbance detection, said system comprising:
   a multi-well plate, said plate adapted to retain a plurality of sample wells;
   a thermal cycler in thermal communication with said multi-well plate;
   at least one photodetector, each said photodetector providing an output signal;
   at least one light source,
   said light source positioned such that light emitted therefrom passes through a corresponding well retained in said multi-well plate and to a corresponding photodetector of said plurality of photodetectors; and
   a means for analyzing said output signals from said at least one photodetector and determining by absorbance detection information indicative of the polymerase chain reaction.

2. The system of claim 1 wherein said light source is selected from the group consisting of light emitting diodes, laser diodes, and combinations thereof.

3. The system of claim 1 wherein said light source emits light having a wavelength in the ultra-violet range.

4. The system of claim 1 wherein said system includes an array of light sources and an array of photodetectors configured to measure the absorbance or fluorescence signal from a plurality of wells, in parallel.

5. The system of claim 1, wherein said at least one light source includes a plurality of closely spaced light sources that sequentially emit light.

6. A system for conducting a polymerase chain reaction assay upon a plurality of samples, said system comprising:
   a multi-well plate, said plate adapted to retain a plurality of sample wells;
   a thermal cycler in thermal communication with said multi-well plate;
   a plurality of photodetectors, each said photodetector providing an output signal;
   at least one ultra-violet light source,
   said at least one ultra-violet light source positioned such that light emitted therefrom passes through a corresponding well retained in said multi-well plate and to a corresponding photodetector of said plurality of photodetectors; and
   a means for analyzing said out put signals from said plurality of photodetectors.

7. The system of claim 6 wherein said at least one ultra-violet light source includes a plurality of ultra-violet light emitting diodes.

8. The system of claim 6 wherein said at least one ultra-violet light source includes a plurality of lasers.

9. The system of claim 6 wherein said light emitted from said ultra-violet light source has a wavelength of from about 175 nm to about 350 nm.

10. The system of claim 9 wherein said wavelength is from about 240 to about 350 nm.

11. The system of claim 6 wherein said at least one ultra-violet light source emits light having a wavelength of 260 nm, 280 nm or a combination of 260 nm and 280 nm.

12. The system of claim 6 wherein said system provides real-time information indicative of the polymerase chain reaction.

13. A spectrophotometer for measuring the intensity of ultra-violet light, comprising:
- a sample well adapted for retaining a liquid sample, said sample well defining a first region and a second region in fluid communication with said first region;
- a photodetector;
- a first ultra-violet light source positioned relative to said sample well and said photodetector such that ultra-violet light emitted from said first light source passes through said first region of said sample well to said photodetector; and
- a second ultra-violet light source positioned relative to said sample well and said photodetector such that ultra-violet light emitted from said second light source passes through said second region of said sample well to said photodetector.

14. The spectrophotometer of claim 13 wherein said first and second ultra-violet light sources are light emitting diodes.

15. The spectrophotometer of claim 13 wherein said first and second ultra-violet light sources are lasers.

16. The spectrophotometer of claim 13 wherein said ultra-violet light sources emit light having a wavelength of from about 175 nm to about 350 nm.

17. The spectrophotometer of claim 16 wherein said wavelength is from about 240 nm to about 300 nm.

18. The spectrophotometer of claim 13 wherein said ultra-violet light source emits light having a wavelength of 260 nm, 280 nm, or a combination of 260 nm and 280 nm.

19. A method of performing a polymerase chain reaction assay by absorbance detection, said method comprising:
- providing a system including (i) a multi-well plate adapted to retain a plurality of samples, (ii) a thermal cycler, (iii) a photodetector that provides an output signal, (iv) at least one light source positioned such that light emitted therefrom passes through said multi-well plate to said photodetector, and (v) a means for analyzing said output signal of said photodetector upon detecting light;
- obtaining samples upon which said polymerase chain reaction assay is to be performed;
- depositing said samples in said multi-well plate;
- performing a polymerase chain reaction in said samples;
- emitting light from said at least one light source such that said light passes through said samples and said multi-well plate to said photodetector; and
- analyzing said output signal of said photodetector to determine the absorbance of light and information indicative of the polymerase chain reaction.

20. The method of claim 19 wherein said method is performed in real-time.

21. The method of claim 19 wherein said light source is selected from the group consisting of light emitting diodes, lasers, and combinations thereof.

22. The method of claim 19 wherein said light emitted from said light source has a wavelength of from about 100 nm to about 400 nm.

23. A method of performing a polymerase chain reaction assay, said method comprising:
- providing a system including (i) a multi-well plate adapted to retain a plurality of samples, (ii) a thermal cycler, (iii) a photodetector that provides an output signal, (iv) a plurality of ultra-violet light sources positioned such that light emitted therefrom passes through said multi-well plate to said photodetector, and (v) a means for analyzing said output signal of said photodetector upon detecting ultra-violet light;
- obtaining samples upon which said polymerase chain reaction assay is to be performed;
- depositing said samples in said multi-well plate;
- performing a polymerase chain reaction in said samples;
- emitting ultra-violet light from said plurality of ultra-violet light sources such that said light passes through said samples to said photodetector; and
- analyzing said output signal of said photodetector.

24. The method of claim 23 wherein said method is performed in real-time.

25. The method of claim 23 wherein said ultra-violet light has a wavelength of from about 175 nm to about 350 nm.

26. The method of claim 25 wherein said ultra-violet light has a wavelength of from about 240 nm to about 300 nm.

27. The method of claim 26 wherein said ultra-violet light has a wavelength of 260 nm, 280 nm, or a combination of 260 nm and 280 nm.

* * * * *